United States Patent [19]

Yao et al.

[11] 4,294,891
[45] Oct. 13, 1981

[54] INTERMITTENTLY REFUELABLE IMPLANTABLE BIO-OXIDANT FUEL CELL

[75] Inventors: Shang J. Yao; Huei Y. Sun Yao, both of Upper St. Clair; Sidney K. Wolfson, Jr., Fox Chapel, all of Pa.

[73] Assignee: The Montefiore Hospital Association of Western Pennsylvania, Pittsburgh, Pa.

[21] Appl. No.: 129,709

[22] Filed: Mar. 12, 1980

[51] Int. Cl.$^3$ .............................................. H01M 8/16
[52] U.S. Cl. .......................................... 429/2; 429/13; 429/29; 429/40; 128/419 B
[58] Field of Search ................................ 429/2, 13–15, 429/29, 40, 46; 128/419 B, 419 P

[56] References Cited

U.S. PATENT DOCUMENTS

| | | | |
|---|---|---|---|
| 3,353,539 | 11/1967 | Pieston | 429/13 X |
| 3,837,922 | 9/1974 | Ng et al. | 429/40 X |
| 3,878,564 | 4/1975 | Yao et al. | 128/419 B X |
| 3,884,243 | 5/1975 | Cywinski | 429/29 X |
| 3,915,749 | 10/1975 | Weidlich | 429/44 |

OTHER PUBLICATIONS

A Single Electrolyte Fuel Cell Utilizing Permselective Membranes, vol. XVI Trans. Amer. Soc. Artif. Int. Organs 1970 pp. 193–198.
A Tissue Implantable Fuel Cell Power Supply, vol. XVI, Trans Amer. Artif. Int. Organs, 1970, pp. 199–205.

*Primary Examiner*—Charles F. LeFevour
*Attorney, Agent, or Firm*—Jacques M. Dulin

[57] ABSTRACT

An implantable biologically acceptable miniature fuel cell that is intermittently refuelable through one or more percutaneously positioned refueling ports. Refueling occurs by injection, preferably by hypodermic, typically annually. No transcutaneous leads or refueling stoma or tubes are employed. The cell is a bio-oxidant cell, as distinct from being a bioautofuel cell, having a silicone membrane coating over at least one external cathode surface permitting oxygen and water molecules to diffuse there through while preventing exit of organic fuel or oxidation-reduction by-products. Carbohydrate fuels are disclosed with glycerol being preferred from among it, glucose, sorbitol and mixtures. A variety of cathode and anode compositions are disclosed with Pt-black anodes and carbon-black cathodes being preferred. A high fuel to $O_2$ concentration ratio is important to prevent $O_2$-parasitic effect on the anode. A high IS buffer is employed as the electrolyte, in the range of above 0.2 M, preferably 0.3–1.0 M, with a pH of above about 6.0, preferably 7.0–7.8. The cells produce approximately 0.14 watt-hr/gm and 0.16 watt-hr/ml, have operated satisfactorily in vitro for 225 days without refueling and are still running, 458 days with refueling, and satisfactorily in vivo for 55 days in baboon subjects without refueling.

14 Claims, 5 Drawing Figures

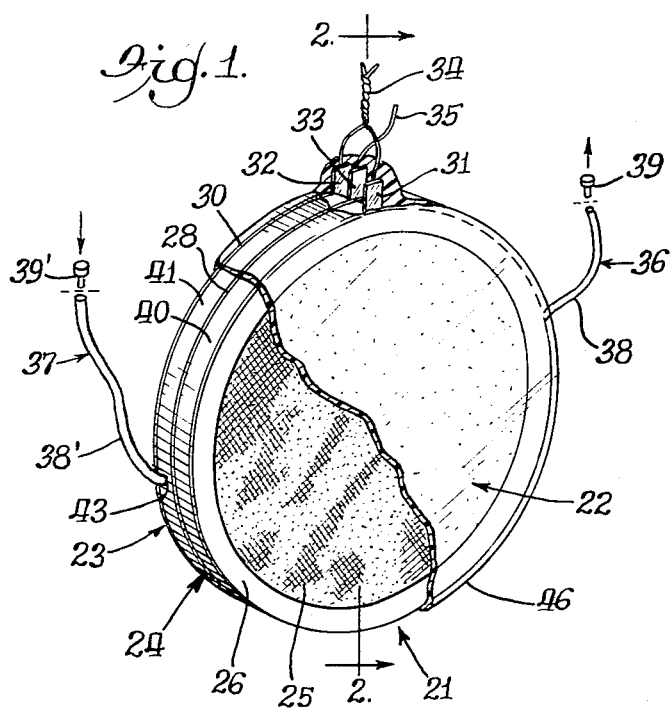
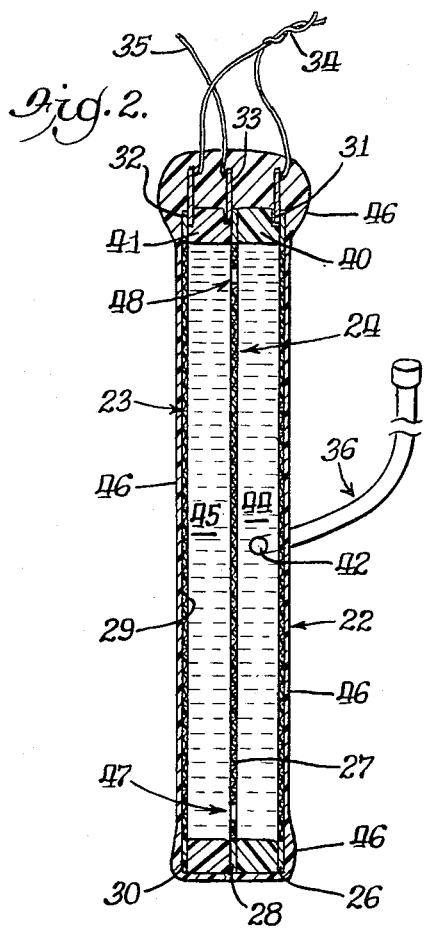
Fig. 1.
Fig. 2.
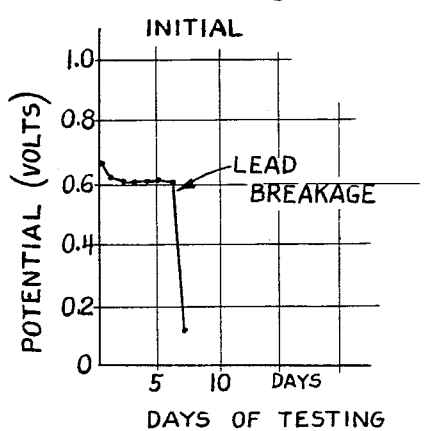
Fig. 4A.
INITIAL
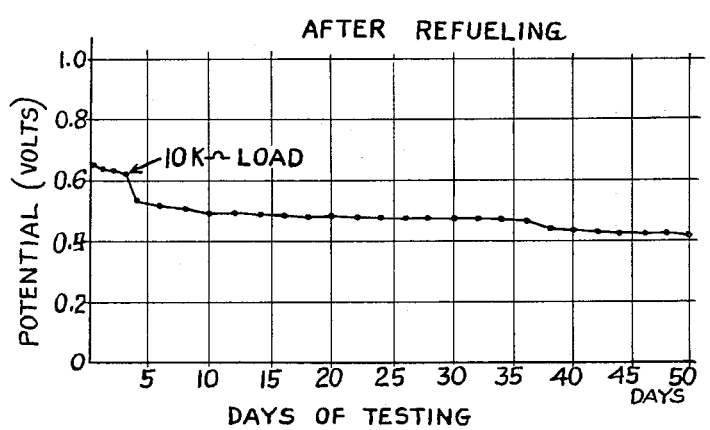
Fig. 4B.
AFTER REFUELING
TEST CELL OF EXAMPLE 5

INTERMITTENTLY REFUELABLE IMPLANTABLE BIO-OXIDANT FUEL CELL

GRANT INFORMATION

The invention described herein was made in the course of work under a grant or award from the Department of Health, Education and Welfare.

FIELD

This invention relates to specialized bio-compatible fuel cells that are implantable into association with biological tissues for powering of electrical or electromechanical prosthetic devices. More specifically, the invention relates to such cells and methods of operation thereof involving specialized cells having means for intermittent refueling and evacuation of spent fuel in combination with biological oxidant source to scavenge electrons at the cathode.

BACKGROUND

Prosthetic devices have been used for hundreds, if not thousands, of years as aids in solutions to certain types of medical problems. In recent bio-medical technology, such prosthetic devices have become far more sophisticated, not only as to scope of problems to which they are applicable, but also in their technological sophistication. Current prosthetic devices rely heavily on electronic or electromechanical activity and, accordingly, need electrical power sources. Because the people requiring the need for such prosthetic devices must carry on an active life requiring mobility, external power sources are impractical. In addition, leads through the skin pose special surgical and bacteriostatic problems. These problems have not yet been solved.

Accordingly, for many years there have been proposed implanted energy sources. Batteries, otherwise known as energy cells, have long been proposed. However, significant problems remain with respect to batteries intended to power such prosthetic devices as cardiac pacemakers, neurostimulators, and physiological monitors. They have also shown to be entirely inadequate for more sophisticated devices on the horizon such as heart pumps and limb activators.

The possibility of utilizing chemical species normally available within the body as reactants for an implantable energy source has been explored for some years. These include the ion concentration cells (1), biochemical fuel cells (2-8), and bio-galvanic cells (9-14). However, all of these types of cells have serious problems which have prevented their practical utilization to any significant extent.

For example, ion concentration cells are limited by concentration differences between different body fluids and, accordingly, cannot produce sufficient or reliable power (15).

Regarding biochemical fuel cells, by taking advantage of biological homeostasis, fuel cells which utilize endogenous compounds could function in principle for a lifetime. Theoretically, the cell volume could be minimized because no reactant storage is required.

Generally, existing energy sources such as energy cells (batteries) must be implanted remotely from the power-requiring device or prosthesis because of their weight and size. The connection between the prosthesis and the battery is provided by electrical leads. However, there has been a frequently reported occurrence of lead failure in existing implantable energy sources (3).

Thus, the proposal for miniature, lightweight energy cells for implantation in direct association with the energy dissipating device (the prosthesis) at its site of action would tend to overcome lead failure problems.

One of the problems with biochemical fuel cells is that the energy generated in chemical reactions of such implantable fuel cells is usually on the order of only 10–100 microwatt ($\mu$-watt). However, such a level is sufficient to power the low-energy demand devices such as the electronic pacemaker (3). Even so, it would not be suitable for more power-hungry devices.

Another problem which has arisen in regard to biochemical fuel cells is their dependence on body fluids which renders them a power supply that is subject to variations in output due to fluctuations in the body's supply of ions, fuels, and oxidants. Since such cells and their electrodes are exposed to numerous components of body fluids, they are difficult to satisfactorily model in vitro, or to translate to in vivo operation. Such cells are called bio-auto fuel cells since they obtain both oxidant and reductant (fuel) from the body. Our previously reported work (3,4,17) on such bio-auto cells demonstrates a full knowledge of in vivo parameters is a necessary prerequisite to design of a satisfactorily functioning cell. These in vivo parameters such as ion, fuel, and oxygen concentration, osmotic pressure, and the like are either unknown or may vary with biological rhythms and implantation sites.

Regarding bio-galvanic cells, previous work since 1971 has been done on an encapsulated bio-galvanic cell (16). The bio-galvanic cell consists of a corroding metal anode and a cathode which utilizes oxygen from the body fluids. Some cells are designed with a "sealed" anode compartment so they do not release toxic products to the body. Other bio-galvanic cells have a corroding metal anode in contact with body tissues. These cells have been subject to uneven and unpredictable electrodissolution of the anode, which has compounded the problem of lead breakage. This longevity is limited by the amount of self-contained reactive metal, and is a function of the weight and dimensions of the cell. If the cell ruptures, toxic products are released in the body.

Accordingly, there is a need for still another approach to providing suitable energy sources which can be satisfactorily encapsulated for implantation in association with biological tissues, that is, are biologically acceptable and non-reactive. These cells must be small and provide sufficient power either by themselves or as a group of cells in a "battery" assembly, as to provide sufficient power for present day and future proposed prostheses. These cells should not be site specific, that is, requiring intimate knowledge of the special biochemical parameters of implantation sites and highly variable biological rhythms of the many different types and conditions of patients into which they are to be implanted. Further, they should be free from lead breakage problem and not be subject to lifetime limitations inherent in original charge of corrodible fuel.

The present invention solves these needs in the form of an intermittently refuelable encapsulated bio-oxidant fuel cell having a self-contained reductant and utilizing endogenous supply of oxygen present in all tissues and which is capable of being refueled and evacuated at infrequent intervals, thereby not requiring an initial charge of fuel for its entire life. In the event of rupture, no toxic fuel or by-products are released into the body.

THE INVENTION

Objects

It is among the objects of this invention to provide a miniature, biologically acceptable, implantable fuel cell which can provide sufficient energy density and power supply to operate current types of prostheses, and which, in multiple assemblies, can provide sufficient energy in the form of a battery pack for future types of prostheses requiring greater power requirements.

It is another object of this invention to provide a special type of implantable fuel cell having a special encapsulation surface which permits diffusion therethrough of oxygen as the oxidant to the cathode, that is, a fuel cell which is of what we call the bio-oxidant type.

It is another object of this invention to provide a miniature biologically implantable encapsulated fuel cell which carries an initial full charge of volume less than that required for the entire life of the cell, but which is also provided with special assembly ports permitting evacuation of spent fuel and introduction of fresh fuel at infrequent intervals as required.

It is an object of this invention to provide a biologically implantable fuel cell which has self-contained reductant fuel and which has excellent longevity features resulting in part to employing an endogenous biological supply of oxygen or other oxidant, and does not pose a danger upon rupture.

It is another object of this invention to provide a special biologically implantable fuel cell which is smaller and lighter than comparable cells of similar energy density.

It is still another object of this invention to provide methods of implantation, refueling and operation of implantable biologically acceptable fuel cells.

Still further and other objects of this invention will be evident from the description and claims which follow.

FIGURES

The invention will be described in more detail in connection with the drawings in which:

FIG. 1 is a perspective view of an encapsulated fuel cell of this invention showing a first, withdrawal, refueling port, and a second, injection port, both optional;

FIG. 2 is a section view of the encapsulated fuel cell through lines 2—2 of FIG. 1;

FIGS. 4A and 4B show performance of another cell after refueling.

SUMMARY

Figure 3:
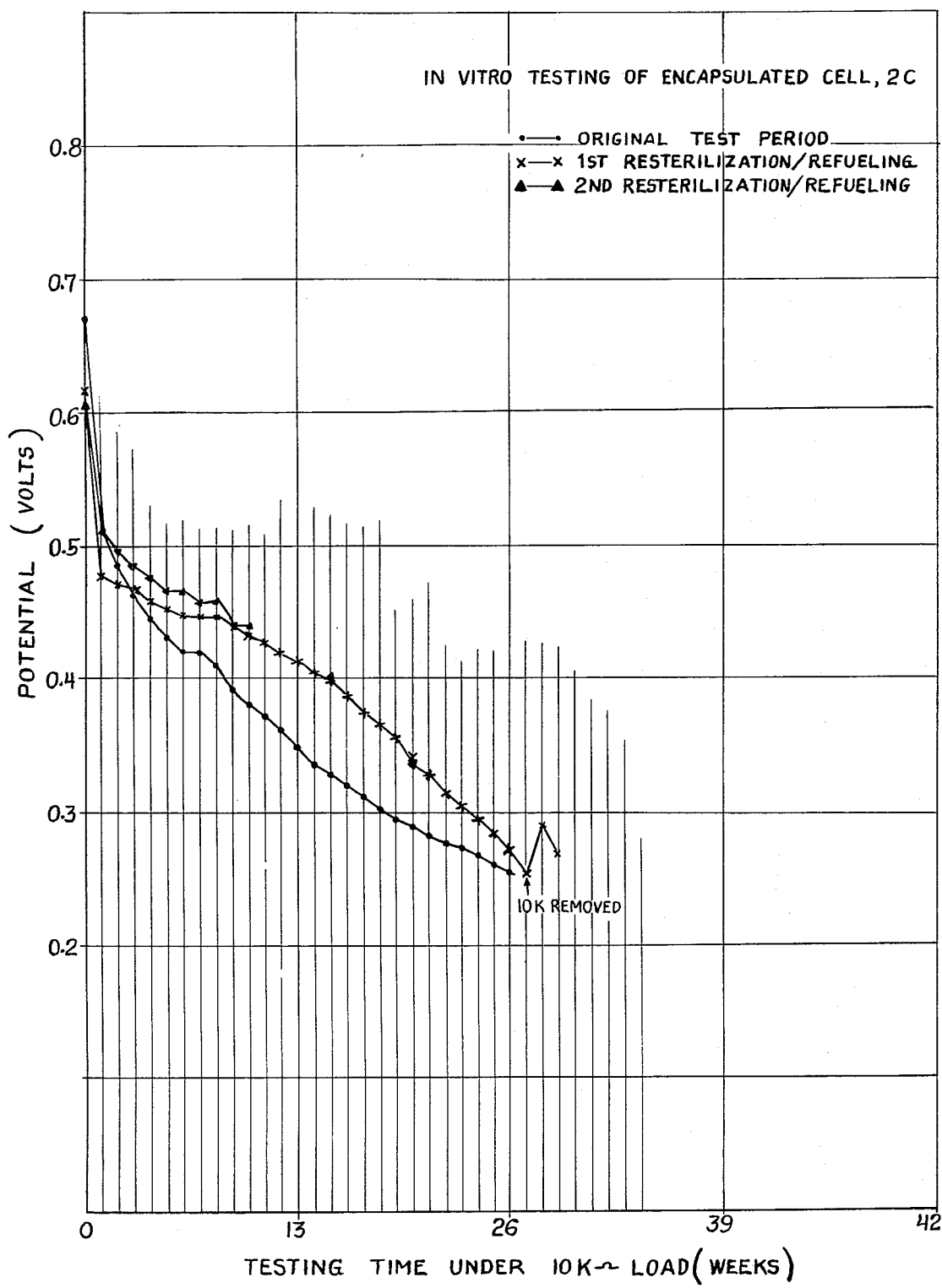
FIG. 3 is a graph showing cell performance and refueling.

The encapsulated biologically implantable fuel cell of this invention comprises, in its presently preferred form, dual porous cathodes having a single platinized anode suspended in the center of a thin fuel/electrolyte chamber. The outer surface of the entire cell is covered by a medical grade silicone rubber which is attenuated to a thin membrane in the areas covering the cathodes. The encapsulated cell requires only oxygen from the surrounding body fluid in which it is implanted. The oxygen diffuses into the otherwise isolated cell through the thin layer of silicone rubber which encapsulates the cell.

Fuel and electrolyte refilling ports are provided, which upon implantation remain below the external surface of the skin, that is, they are subcutaneously placed in a predetermined place to be accessible to penetration by a hypodermic needle and syringe. By this method, fresh fuel and/or electrolyte can be intermittently resupplied, and the longevity of the cell is extended indefinitely. The cell is thus an electrically independent unit which does not require any ionic contact with tissue electrolyte or long leads to the prosthesis which it is to power. Accordingly, two or more cells may be connected in series to form a battery having higher voltage, for example, on the order of greater than 1 volt, which are thus highly suitable for electronic circuit design. Miniaturization of the encapsulated fuel cell results from the cell requiring only a small amount of fuel to sustain the necessary length of operation, e.g., 1 year. Optionally, for longer operation, intermittent (e.g., annual) percutaneous refueling may be done. The refueling procedure is much easier, less expensive and medically far safer than the repetitive surgical replacement of batteries of current available devices.

In the cell, ionic conduction occurs through the liquid electrolyte in which the fuel is dissolved. The electrolyte is highly concentrated and conductive to minimize the IR drop in the solution. The use of concentrated electrolyte also minimizes the migration of the reactant or product ions due to the electric field. Fuel compounds and electrolytes can be varied and optimized under rigorous controls in vitro prior to application to in vivo use. The pH and buffering capacity of the solution is also controlled.

The fuel may be any catalytically oxidizable, nonvolatile and nontoxic compounds, the waste products of which cannot rediffuse back through the silicone membrane encapsulating the cell. Presently preferred fuels are carbohydrates and the most preferred is glycerol because it has a relatively small molecular weight (92 daltons), which provides a very favorable molecular concentration/mass ratio. Glycerol also possesses a high diffusivity at the electrode. A cell containing 5 ml of a 2.7 M glycerol solution having 12 available electrons per molecule for oxidation is capable of supplying a power output of $50\mu$-watt at 0.5 volts for five years. The electrochemical reactions for the glycerol fuel cell of this invention are as follows:

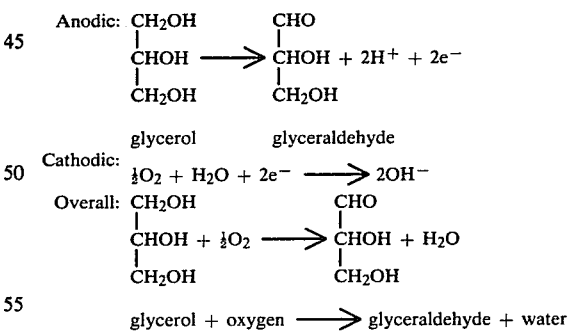

The present invention also has the advantage of permitting oxygen-to-fuel concentration ratio being varied by changing the preloaded fuel concentration. This is important because in this type of cell the oxidant has entry to the anode portion of the cell. By having highly concentrated fuel as compared to oxygen, the maximal coverage of the anode catalytic surface by fuel is accomplished. The intermittent refueling removes products formed on the catalytic sites and re-establishes the concentration of fuel at the electrode surfaces, thus regenerating the activity of the anode catalyst. Accordingly, the parasitic effect of oxygen on a platinum black anode which has been observed in bioautofuel cells (17) is overcome. In the bioautofuel cell, where the ratio of oxygen to glucose was 1:50, the oxygen gradually replaced the adsorbed glucose and caused deterioration in the anode function. The present invention overcomes this disadvantage, and also eliminates the adverse effects of co-reactants (18) and chloride ions present in tissue fluids.

The method of the invention includes providing the specialized cell assembly and functions and implanting the cell, either precharged or charging it after implantation. The implantation is done in a manner which positions the one or more withdrawal or injection ports (the refueling ports) beneath the skin surface so there is no bacterial infection, and so there is relatively static and permanent positioning of the ports for subsequent refueling on the order of once annually. The fuel cell is connected with a prosthetic device which it powers. A plurality of cells can be hooked up in series to provide higher voltage.

DETAILED DESCRIPTION

The following detailed description is by way of example and not of limitation of the principles of the present invention.

FIG. 1 shows in perspective a fuel cell assembly 21 which comprises a pair of cathode assemblies 22 and 23 disposed spaced on each side of an anode assembly 24. The cathode assembly was a gold-black/Teflon paste (75% Au; 25% Teflon) within an expanded gold mesh current collector. Typically, the cathode paste contains 30 mg Au/cm$^2$. This current collector cathode assembly 25 is secured to a flat annular ring 26. Similarly, the anode is a platinum-black electrode composition having 15 mg Pt/cm$^2$ of 75% Pt, 25% Teflon pressed into an expanded gold mesh current collector. This assembly 27 (see FIG. 2) is also secured to a flat annular framing ring 28. The second cathode assembly 23 likewise comprises a gold current collector mesh having a gold-black electrode composition 29, as described above, supported in annular framing ring member 30. Cathode tabs 31 and 32 and anode tab 33 are attached to the gold mesh current collectors and in turn connect to leads 34 and 35 passing to the prosthetic device to be powered.

In one embodiment, short filling tubes are provided in apertures 42 and 43 through which the sterilized cell is fueled. After fueling, plugs are placed in the tubes for a permanent seal. This embodiment is suitable for cells that are for short-term use, i.e., need not be refueled.

For long term cells, at least one refueling port assembly 36 or/and 37 is provided. These port assemblies comprise a tube 38 or 38', the upper end of which is sealed by a multiply penetrable but self-sealable, non-leaking port 39 or 39'. The tubes are secured into frame sections 40 and/or 41 and provide a passageway through aperture 42 (FIG. 2) or/and corresponding aperture 43 into the electrolyte chambers 44 and 45 defined between the ring-like spacer frame members 40 and 41 and the anode and cathode assemblies 22, 23 and 24. The port members 39 and 39' are of a type which can be pierced by hypodermic needles. The tube members 38 and 38' may be of equal or differing lengths and are of sufficient length to position the plug members below but adjacent to the skin surface as is predetermined by the necessary positioning of the fuel cell assembly and the prosthetic device (not shown) which it powers. The entire assembly is coated with a medical grade silicone rubber. For example, we prefer to use medical adhesive silicone type A silicone elastomer "SILASTIC" brand made by Dow Corning, or an RTV of silicone rubber made by General Electric Corporation. Any coating material which is biocompatible, nonreactive, tissue acceptable, and permitting oxygen diffusivity therethrough may be used. It also must prevent the diffusion outwardly from the electrolyte chambers 44 and 45 of either the electrolyte/fuel solution or any toxic oxidation/reduction products. That is, the cell must be entirely sealed except for oxygen diffusion through the exterior coating 46.

To permit full flow of electrolyte from one chamber 44 into chamber 45, one or more apertures 47 and 48 may be provided in the anode assembly. This is an option which may not be required as the platinum black/Teflon compound as loaded into the gold current collector will still permit flow of electrolyte/fuel solution between the two chambers.

Exhausted electrolyte/fuel compositions may be first withdrawn by hypodermic syringe from the cell electrolyte chambers and thereafter refilled through the same port, while the second port is open to the air, e.g., via a second needle. We prefer to inject fresh fuel/electrolyte solution through one port such as injection port 37, while simultaneously letting spent electrolyte/fuel solution be forced out through the other port 36 into a second hypodermic. While the apertures 42 and 43 are shown on the side of the fuel cell assembly, it should be understood that they may be placed at the lowest point of the implanted cells orientation. We presently prefer to fill (refuel) from the bottom and withdrawn from the top of the cell. This is to permit complete filling of the cell and avoid formation of air bubbles. As shown in FIGS. 1 and 2, the side inlet position of the refueling port assemblies 36 and 37 is particularly suitable where the assembly is placed with the plane of the disc in a horizontal position in the body.

The electrolyte/fuel solution preferably is an aqueous buffer solution serving as the internal electrolyte plus a non-volatile, organic fuel, such as carbohydrates, non-toxic polyhydric alcohols, acetates and the like. We presently prefer fuels selected from glycerol, glucose, sorbitol and mixtures thereof, in amounts ranging from 10–50 g/dl, preferably 25 g/dl. The electrolyte buffer solution is 0.2–1.0 M phosphate buffer of pH 7.0–7.8, most preferably 0.3–0.6 M at a pH of substantially 7.4.

As disclosed in more detail below, encapsulated fuel cells were constructed and tested both in vitro and in vivo, including complete refueling. These cells had the following characteristics: The electrode diameters were 3.1 cm with the overall cell diameter being 4.2 cm. The cell thickness was 1.0 cm, and the fuel reservoir volume was 5 ml. They consisted of a single platinum-black anode (Energy Research Corp., 30 mg Pt/cm$^2$, 75% Pt/25% Teflon) and two carbon black cathodes. The cathodes were prepared from a mixture of activated carbon (Pittsburgh Activated Carbon Co.) and Teflon resin 6-C (du Pont), 75% C/25% Teflon. The platinum black anode composition in its gold mesh current collector was suspended between the two cathodes, likewise being the cathode composition described above loaded into the gold mesh current collectors. The two cathodes are separated from the anode by polyethylene rings which provided the space for the fuel reservoir. The cathodes also function as the outer walls of the cell, which was then painted over with a thin layer of silicone rubber, Silicone Type A-891.* The entire cell assembly was then sterilized by autoclaving. In the examples below, the cells were fueled with sterile solutions of 25 g/dl glycerol, glucose or sorbitol in 0.3 M or 0.6 M phosphate buffer at pH 6.0 or 7.4. For the in vitro testing, the cells were placed in chambers containing Krebs-Ringer bicarbonate buffer of pH 7.4 at 37° C. and gassed with 85 torr $O_2$ and 35-40 torr $CO_2$ to simulate physiological conditions. Although not required for function of the cell, the gases entered and exited the chamber through bacterial filters to avoid contamination of the sterile environment.

*Dow Corning

Three types of encapsulated cells were then prepared for in vivo evaluation.

These cells had the same dimensions as the in vitro cells tested. They each had platinum-black anodes with either 2 Ag-black, or 2 Au-black, or 2 carbon-black cathodes. After autoclaving or soaking in 10% KOH, bacterial cultures were taken to confirm sterility. Each cell was implanted into the peritoneal wall of a baboon. Two methods were used to measure implanted cell voltages. Some baboon subjects were placed in primate restraint chairs with percutaneous leads from the fuel cell for continuous voltage monitoring. At other times, baboons were monitored intermittently and were unrestrained in their cages between measurement periods. We currently use telemetry for continuous monitoring of the cell output.

SPECIFIC EXAMPLES

The following specific examples demonstrate various configurations of cells of this invention and the operational results, in vitro and in vivo, and refueling.

EXAMPLE 1

This example demonstrates the criticality of a high fuel to $O_2$ ratio to overcome the $O_2$-parasitic effect on the anode, here a platinum-black anode. The cell is as described above with the $O_2$ being at the highest normal body tissue $O_2$ level, i.e., a $PO_2$ around 85 torr (dissolved $O_2$ around 0.1 mM). The electrolyte in all cases was an aqueous solution of a 0.3 M phosphate buffer, chloride free, pH 7.4.

A comparison or standard cell was prepared using glucose as the fuel in the electrolyte solution at the normal physiologic level of 5 mM, 90 mg/dl The anode voltage of this cell decayed rapidly over about 90 hours at 50 $\mu$amp, from $-0.36$ v vs Ag/AgCl to a more cathodic value of $-0.10$ v, clearly indicating the pronounced $O_2$ —parasitic effect. This cell was deemed inoperative due to the rapid $O_2$ —parasitic failure.

Test cell A was fueled with 2700 mM glycerol (25 g/dl) in the electrolyte and the OCV of the whole cell was constant for a six-hour test period at 0.53 v. Then, under 10 K-ohm load, the whole cell voltage dropped to a constant 0.34 v. The anode half-cell voltage remained constant at $-0.3$ v vs. Ag/AgCl. A relatively constant power output of 11.5 $\mu$-watt was maintained for 60 days with the 10 K-ohm load.

Other test cells were fueled with various fuel concentrations as follows:

TABLE I

| | Fuel | $O_2$ | Concentration Ratio | Result |
| --- | --- | --- | --- | --- |
| Normal | 5mM | 0.1mM | 50:1 | Failed |
| Test Cell B | 5mM | 0.04mM | 125:1 | Failed |
| Test Cell C | 5mM | 0.01mM | 500:1 | Failed |

TABLE I-continued

| | Fuel | $O_2$ | Concentration Ratio | Result |
| --- | --- | --- | --- | --- |
| Test Cell A | 2700mM | 0.1mM | 27,000:1 | Excellent |

These tests show it is critical to keep the fuel: $O_2$ ratio above about 500:1.

EXAMPLE 2

This example demonstrates the in vitro performance of an encapsulated glycerol-fuel cell in accordance with this invention having two carbon cathodes. The carbon cathodes may either be carbon black plus Teflon in the ratio of 75 to 25 weight % in paste form filled in a gold mesh current collector, or carbon black in an acrylic polymer painted on the gold mesh current collector. The cell was otherwise as described above. The open circuit voltage of the entire cell was 0.68 v. Under a constant 10 K-ohm load, the whole cell voltage gradually fell from 0.45 v (20 micro-watts) on the 25th day of continuous operation to 0.28 v (9.2 micro-watts) on the 150th day of continuous operation. As shown in other tests, the voltage would have been maintained at a higher level if the cell has been placed on pulsed or intermittent load. A typical pulsed system would be 75 cycles per minute, 50%, "on" and 50% "off". Under pulse load system of this type, the energy drain to the dissipating system (the electronic electrical or electromechanical prothesis) occurs in an intermittent manner rather than in a constantly "on" manner as in the above example. The "off" mode (open circuit) affords an opportunity for the cell to recover. During the 160 days of operation, at the end of which the cell test was terminated, the cell outer walls (the cathodes 22 and 23 as shown in FIGS. 1 and 2) became externally convex demonstrating cell expansion. The fact that the entire cell will permit some expansion is a safety feature. The cell, being encapsulated in silicon rubber is permeable to gaseous molecules such as $O_2$, $CO_2$ and water vapor. The silicon rubber encapsulated layer (see element 46 in FIGS. 1 and 2) is sufficiently flexible to compensate for this cell expansion without pin holes or rips occuring in the coating, that is, the silicon rubber coating retains its integrity.

The concentration ratio of the internal fuel electrolyte, being around 3 osmolar, to the Krebs-Ringer bicarbonate buffer, being about 0.3 osmolar, that is, a ratio of 10 to 1 creates a driving force for the water vapor to diffuse into the cell. Over a period of time the influx of water may increase the volume and distends the somewhat elastic cathode walls of the cell. Under certain cell configurations, this outward force on the cathodes could lead to partial separation of catalyst and current collector resulting in an increase in electrode resistance and decaying cell voltage. To minimize this situation, the cells may be kept small, the osmotic imbalance may be minimized by decreasing the concentration of the fuel, but it must always be kept above the level below which oxygen poisoning of the anode occurs.

Still another approach is to only partially fill the cell leaving a disengagement space above the liquid fuel-/electrolyte level in the cell which optionally may be filled with carbon dioxide or other nontoxic inert gas. This may be easily accomplished by partially filling the cell through the refueling port, e.g. the injection port 37, while withdrawing excess $CO_2$ as the cell fills. After injection of $CO_2$ into the cell, as the cell then equilibrates in situ the balance of the $CO_2$, $N_2$ etc, can migrate out of the cell. In still another alternative design, the mechanical strength of the cell is increased by providing an exterior cage, preferably of plastic and preferably a sheet having holes (not shown) so that as the system develops internal pressure the outward movement of the cathode assembly as coated with the silicone presses against the rigid external surface. The exterior support means may also be coated with the silicone to insure that it is bio-acceptable.

In test cell 2A a single Pt-black anode was sandwiched between two Ag-black cathodes. The fuel was 25 mg/dl glucose in 0.1 M phosphate buffer at pH 6.0. The cell started out with open circuit voltage between 0.6–7 v and dropped quickly (within a day) to around the 0.3 v level. The voltage continued to drop to around the 0.19 v level at around 20 days, and recovered to the level of around 0.25–30 through the 45th day. Lead breakage occurred at that time, and the voltage dropped to about 0.03 v. Dissolution of silver into the internal electrolyte was observed, and while we do not wish to be bound by theory, we believe it to be the major cause of the failure of that cell.

Test cell 2B in this Example 2 series was constructed with a Pt-black anode and a single Au-black cathode (both with gold current collector). It should be noted that "gold black" is the generally accepted term in the art for finely divided gold used in the paste composition with Teflon in the ratio of 75% Au to 25% Teflon, and presents a brownish appearance. The fuel was 25 g/dl glucose in 0.1 M phosphate buffer at pH 6.0. This cell also exhibited poor performance from approximately similar open cell voltage drifting downwardly from the level of 0.5 v after approximately one day to 0.21 v at about 24 days. Some irregularity in voltage was experienced in the level between 0.2–28 v through the 35th day at which time the voltage dropped off rapidly to 0.01 v at the 48th day. This cell was not deemed satisfactory.

In both of these test cells 2A and 2B, the pH of the internal fuel/electrolyte solution was found to be very acidic, that is, a pH of 2.0–3.0 when the cell was terminated because of poor performance at around 50 days.

The products of glucose oxidation under the conditions of operation of the cell are proposed as gluconic acid and/or glucuronic acid which accordingly may be the cause of the pH drop. Such a pH change has not been observed in the cells of this invention employing glycerol as the fuel, and accordingly, glycerol is the preferred fuel, that is, the currently preferred best mode of practicing the invention. While we do not wish to be bound by theory, we believe that the reason for lack of such a pH change in the glycerol-fueled cells is that the oxidation product is glyceraldehyde which is not acidic. In addition, the internal electrolyte used in the glycerol cell has a greater buffering capacity of 0.3 M as compared to the 0.1 M phosphate buffer used in the cells 2A and 2B. Further, the initial pH of the glycerol cell is set at 7.4 as compared to 6.0 for cells 2A and 2B.

Cell 2C was constructed utilizing a platinum black anode and two carbon black cathodes. Like cell 2B, the cathode current collector is a gold mesh. Again, the fuel was 25 g/dl glycerol and 0.3 M phosphate buffer with an initial pH of 7.4. This cell demonstrated relatively high open circuit voltage, 0.3 v vs. Ag/AgCl, and maintained higher cathodic voltage, 0.1 v vs. Ag/AgCl, under a constant 10 K-ohm load. The OCV of the whole cell started at the 0.6–0.7 range, and only gradually drifted down in a relatively smooth curve to around 0.28 v by the end of the test, 158 days.

FIG. 3 illustrates the performance of Cell 2C over a 458-day period, fueled initially, and refueled after each time the cell voltage dropped to an arbitrary 25 volt figure. The cell exhibits excellent performance under rigorous conditions for constant 10 K-ohm load.

In all testwork in this Example 2, the fuel cells were submerged in Krebs-Ringer bicarbonate buffer at 37° C. and gassed with 12% $O_2$, 5% $CO_2$, and 83% $N_2$.

Table II below shows a summary of the operation of test cells 2C through 2I employing various types of fuel cell electrodes and fuels. All cells were tested in vitro under the conditions described above and with the fuel volumes and buffers described previously.

TABLE II

SUMMARY OF ENCAPSULATED FUEL CELL TESTING

| Fuel Cell Electrodes | Cell No. | Encapsulated Fuel, pH | No. Tested | Days Under 10K-OHM Load With Power Output > 10 μWatt | > 5 μWatt | Duration of Testing |
|---|---|---|---|---|---|---|
| 2 Gold Cathodes, Platinum Anode | 2D | Sorbitol pH 7.4 | 1 | 7 days | 9 days | 40 days |
|  | 2E | Glycerol pH 7.4 | 1 | 10 days | 10 days | 28 days |
|  | 2F | Glucose pH 6.0 | 1 | 6 days | 11 days | 28 days |
| 1 Gold Cathode, Platinum Anode | 2G, H | Glucose pH 6.0 | 2 | 3 days 2 days | 26 days 23 days | 26 days 51 days |
| 2 Silver Cathodes Platinum Anode | 2I | Glucose pH 6.0 | 1 | 17 days | 35 days | 48 days |
| 2 Carbon Cathodes Platinum Anode | 2C | Glycerol pH 7.4 | 1 | 112 days* | 160 days | 458 days** (still functioning) |

*This is initial period. Power output >20 μwatt for 25 days.
**Cell refueled 3 times. Upon each refueling, cell restored to approximately 28-30 μwatts. Excellent cell operation.

EXAMPLE 3

In this example, a series of three cells was constructed and evaluated after implantation.

Test cell 3A was constructed of a platinum black anode with two gold black cathodes and loaded with 25 grams per deciliter glycerol in 0.3 molar phosphate at pH 7.4. This cell was then implanted into the peritoneal cavity of a baboon. In vitro preimplantation evaluation gave an open cell voltage of 0.53 volts, and following one hour under a 10 K-ohm load, the voltage dropped to 0.47 volts. Immediately after implantation, the cell tested with an OCV of 0.49 volts. Under a constant 10 K-ohm load, the cell voltage fell gradually to 0.20 volts on the 19th day postimplantation. The voltage remained at 0.20 volts until the 28th day. It delivered a constant power output of four microwatts during this period. The cell was terminated due to cathode lead corrosion. A slight cell volume expansion was observed due to the osmotic imbalance described above without harm to the subject. During the implantation period, the cell voltage rhythmically cycled about 0.05 volts during the course of a day. The voltage peaked around 4:00 p.m. and bottomed around 3:00 a.m. While we did not definitely correlate these rhythmic cell voltage variations to biological parameters, and do not wish to be bound by theory, it is likely that changes in $PO_2$ metabolism and/or body temperature may be responsible. A variation of endogenous $PO_2$ due to changes in metabolism or respiration could affect the $PO_2$ concentration reaching the cell. Cell voltage may also vary with temperature changes as the rates of chemical reactions depend upon temperature.

The other two cells, 3B and 3C, as well as the results of 3A, are summarized in Table III below.

TABLE III

"IN VIVO" TESTING: FUEL CELLS IMPLANTED IN PERITONEAL CAVITY OF BABOONS

| Cell No. | Fuel Cell Electrodes | Encapsulated Fuel, pH | No. Tested | Days Under 10K-OHM Load with Power Output | | Duration of Testing |
|---|---|---|---|---|---|---|
| | | | | >10 μWatt | >5 μWatt | |
| 3A | 2 Gold Cathodes, Platinum Anode | Glycerol pH 7.4 | 2 | 3A 3 days | 6 days | 19 days |
| 3B | | | | 3B 8 days | 17 days | 37 days |
| 3C | 2 Silver Cathodes, Platinum Anode | Glucose pH 6.0 | 1 | 3C 26 days | 36 days | 120 days |

EXAMPLE 4

In this example, the reproducibility, stability and effect of electrolyte ionic strength (IS) under the conditions of open circuit (OC), constant 10K-ohm load, and pulsed (intermittent) load were examined. The intermittent load pulsing was 30% at 10K-ohms followed by 70 percent open circuit at the rate of 17 cycles per second. A 10K-ohm load is an acelerated harsh test condition.

Six cells, test cells 4A–4F of identical electrode and frame construction were used. The cells contained an internal platinum black anode and two carbon black cathodes which functioned as the external walls of the cell. The cell was encapsulated in a very thin coat of silicone rubber, on the order of 3 to 6 mils, permeable as above described to gases and water vapor. To minimize swelling due to osmotic imbalance, the outer surfaces of both cathodes were supported by perforated Lexan plastic plates. The cells were fueled with 5 ml glycerol (25 gm/dl), in either 0.3 M or 0.6 M chloride-free phosphate buffer solution having a pH of 7.4. As noted above, the buffer served as the internal electrolyte.

These cells were then tested in a 37° C. bath containing KRBB (Krebs-Ringer Bicarbonate Buffer), with $PO_2$ at around 85 torr, $PCO_2$ around 40 torr, and pH 7.4. The open circuit voltage of the cells range from 0.63 volts to 0.75 volts.

Two of the cells served as controls, cells 4A and 4B, and had steady OCV of 0.65 volts for more than 200 days, demonstrating stability and reproducibility. The other 4 cells, test cells 4C through 4F, were placed under 10K-ohm load for 50 days. Their potentials fell almost identically from the 0.65 volts, open cell voltage to 0.55 volts at 30 microwatts, and stabilized at this potential in less than 50 days again demonstrating reproducibility and stability of these cells under load.

Two cells, 2E and 2F, were then placed under pulsed load after the fiftieth day. Both under constant and pulsed loads, the cells containing the higher IS buffer, 0.6 M, performed significantly better than the corresponding cells with the IS, 0.3 M, for a 260-day testing period. Cells with the higher IS buffer consistently exhibited greater power output at higher potentials.

EXAMPLE 5

Test cell 5 performed exceedingly well while implanted with an output of 34 μW for a week after which one of the cathode leads fractured. This cell, constructed in the carbon cathode/Pt anode/carbon cathode format, was fueled with 5 ml of 25 g/dl glycerol in 0.3 M phosphate buffer pH 7.4. The OCV immediately after filling the cell was 0.795 V. Prior to implantation, the cell was maintained under open circuit conditions for a month. At the time of implantation, the OCV was 0.649 V and it had been stable at that potential for at least one week. When both transmitter and fuel cell were in position in the peritoneal cavity of a baboon, the fuel cell OCV remained at 0.650 V. A 10 K ohm load was applied and in 30 minutes the voltage dropped to 0.608 V. By the 6th day post-implantation, the cell voltage under 10 K ohm load had dropped to 0.585 V (34 μW). On the 7th day, the cell voltage abruptly fell to 0.115 V, FIG. 4A. The cell and the transmitter were left in the baboon for 7 months to test the body tolerance of the implants and the transmitter performance. When removed, the performance monitoring transmitter was no longer functioning. The silicone tubing covering one of the leads was filled with bloody fluid and this leakage may have caused the cell failure. The inside of the cell was flushed thoroughly with KRBB. No leaks in the cell body were detected. It was emptied and the silicone rubber cut away from the tab end and leads. That area was cleaned with absolute alcohol and air dried; the lead wires were reconnected and the tabs re-coated with silicone adhesive. The cell was then steam autoclaved and refueled with 25 g/dl glycerol in phosphate buffer, (pH 7.4). It had an OCV of 0.64 V. It required fifty days for the cell voltage, under 10 K ohm load, to fall to 0.40 V, 16 μW, See FIG. 4B.

EXAMPLE 6

In this working example, a battery can be assembled from four miniaturized cells containing 1 ml of fuel each. These cells in series yield approximately 150 microwatts at approximately 2 volts.

This battery assembly may be refueled after implantation as described above. Such a battery assembly may be used as a life-long energy source for implantable devices. The cells may also be connected in parallel, or partly in series partly in parallel.

The encapsulated fuel cells of this invention containing approximately 5 ml of 25 grams per deciliter glycerol are calculated to produce a power of 50 microwatts at 0.5 volts for 5 years. Inclusive of the weight and volume of the case, the electrodes and fuel, such cells have an energy density of 0.14 watt-hr/gram and 0.16 watt-hr/ml. These compare very favorably to the lithium batteries (19,20) under current development and evaluation. Lithium cells are projected to have a lifetime of 10 to 15 years, and an energy density of 0.11 watt-hr/gram and 0.25 watts-hr/ml. However, the lithium cells contain toxic volatile or dangerous compounds and must be hermetically sealed. In contrast, the encapsulated cells of this invention do not contain toxic volatile or dangerous compounds and do not require hermetic sealings. The unique refuelable feature of the present invention permits it to have an indefinite lifetime, permits miniaturization while being lightweight and simple of construction. In addition, the cell is also suitable for short-term use, such as perinatal and perioperative implantable monitoring devices. Herein we used 10 K-ohm loads for virtually all cell evaluation. As this causes a higher current draw than anticipated in cell usage, it represents an accelerated drain, and therefore an accelerated test. Accordingly, at more realistic test loads such as 50 K-ohms, the cells of this invention would show even better voltage characteristics over a longer time.

The anode metal loaded into the current collector is to be finely divided or in Rainey-type form. The anode metal may be Platinum, Palladium, Ruthenium, Rubidium, Iridium, Nickel, alloys, and mixtures thereof. Although we presently prefer Platinum black. The cathode metal is selected from gold, silver carbon in finely divided form and we prefer carbon black. The aqueous electrolyte solution includes any inorganic chloride-free buffer in pH range of 7.0–7.8, such as sodium monobasic phosphate, sodium bicarbonate equilibrated with phosphate or $CO_2$ to the pH range, tris (hydroxymethyl) aminomethane and the like.

It should be understood that various modifications within the scope of this invention can be made by one of ordinary skill in the art without departing from the spirit thereof. For example, cathode and anode paste compositions or loadings other than 30 or 15 mg metal $cm^2$ may be used, and current collectors such as Tantalum may be employed. We therefore, wish our invention to be defined by the scope of the appended claims as broadly as the prior art will permit, and in view of this specification if need be.

REFERENCES

1. Rehm, W. Stomach production of electrical energy. Am. J. Physiol., 154:148, 1948.
2. Warner, H. and Robinson, B. W. A glucose fuel cell. Digest 7th Int. Conf. Med. Biol. Eng., 1967, p. 530.
3. Wolfson, S. K., Jr., Gofberg, S. L., Prusiner, P., and Nanis, L. The bioautofuel cell: A device for pacemaker power from direct energy conversion consuming autogenous fuel. Trans. Am. Soc. Artif. Intern. Organs, 14:198, 1968.
4. Wolfson, S. K., Jr., Yao, S. J., Geisel, A., and Cash, H. R., Jr. A single electrolyte fuel cell utilizing permselective membranes. Trans. Am. Soc. Artif. Intern. Organs, 16:193, 1970.
5. Drake, R. F. Implantable fuel cell for an artificial heart. Proc. Artif. Heart Program Conference, Washington D.C., 1969, p. 869.
6. Drake, R. F., Kusserow, B. K., Messinger, S., and Matsuda, S. A tissue implantable fuel cell power supply. Trans. Am. Soc. Artif. Intern. Organs, 16:199, 1970.
7. Rao, J. R., Richter, G., von Sturm, F., and Weidlich, E. Biobrennstoffzellen als stromquellen fuer implantierte elektronische geraete, Ber. Bunsen-Gesel. Phys. Chem., 77:787, 1973.
8. Rao, J. R. and Richter, G. Implantable bio-electrochemical power sources. Naturwissenschaften, 61:200, 1974.
9. Roy, O. Z. and Wehnert, R. W. Keeping the heart alive with a biological battery. Electronics, 39:105, 1966.
10. Strohl, C. L., Scott, R. D., Frezel, W. J., and Wolfson, S. K., Jr. Studies of bioelectric power sources for cardiac pacemakers. Trans. Am. Soc. Artif. Organs, 12:318, 1966.
11. Konikoff, J. J. In vivo experiments with the bioelectric potentials. Aerospace Med., 37:824, 1966.
12. Schaldach, M. and Kirsch, U. In vivo electrochemical power generation. Trans. Am. Soc. Artif. Intern. Organs, 16:184, 1970.
13. Schmuckler, R., Beard, R. B., Dubin, S. E., Sypniewski-Radovsky, A., and De Rosa, J. Power output of implantable hybrid power sources in a low oxygen tension environment. Proc. 27th Ann. Conf. on Eng. Med. Biol., 16:4, 1974.
14. Rao, J. R., Richter, G., and von Strum, F. Metal-oxygen and glucose-oxygen cells for implantable devices. Biomed. Eng., 9:98, 1974.
15. Roy, O. Z. The current status of cardiac pacing. CRC Crit. Rev. Bioeng., CRC Press, 12(3):259, 1975.
16. Tseung, A. C. C. and King, W. An encapsulated implantable metal-oxygen cell. Med. Biol. Eng., 9(3):175, 1971.
17. Yao, S. J., Wolfson, S. K., Jr., Tokarsky, J. M., Liu, C. C., and Weiner, S. B. The effect of $O_2$ on the Pt-black anode of implantable fuel cells. Proc. 29th Ann. Conf. Eng. Med. and Biol., 18,427, 1976.
18. Gough, D. A., Anderson, F. L., Giner, J., Colton, C. K., and Soeldner, J. S. Effect of coreactants on electrochemical glucose oxidation. Anal. Chem., 50:941, 1978.
19. Greatbatch, W., Lee, J. H., Mathias, W., Eldridge, F., Moser, J. K., and Schneider, A. A. The solid state lithium battery: A new improved chemical power source for implantable cardiac pacemaker. IEEE Trans. Biomed. Eng., Vol. BME 18(5):317, 1971.
20. Greatbatch, W. A double-anode lithium iodine cell for implantable cardiac pacemakers. Dig. 10th Int. Conf. Med. Biol. Eng., 1973, p. 340.

We claim:
1. A biologically acceptable, implantable, bio-oxidant fuel cell comprising in operative combination:
 (a) at least one anode assembly;
 (b) at least one cathode assembly;
 (c) a fuel/electrolyte chamber defined between said anode and said cathode assemblies for receiving an externally supplied fuel;
 (d) an electrical lead attached to each of said anode and cathode assembly to provide electrical output to a prosthesis;
 (e) a biologically acceptable, oxygen permeable membrane disposed substantially in contact with said cathode assembly so that said membrane lies between said cathode and body tissue, said membrane being adapted to permit endogenous tissue $O_2$ as a biological oxidant to diffuse into said cell from said body tissue;
(f) a fuel/electrolyte composition disposed in said fuel/electrolyte chamber; and
(g) said fuel/electrolyte composition having a high concentration ratio of fuel to endogenous tissue $O_2$ diffusing through said membrane into said cell.

2. A bio-oxidant fuel cell as in claim 1 wherein:
(a) the fuel to oxygen concentration ratio in said fuel/electrolyte composition is above about 500 to 1 and is an organic, non-volatile fuel.

3. A bio-oxidant fuel cell as in claim 2 wherein:
(a) said electrolyte is a chloride-free buffer having an ionic strength above 0.2 molar.

4. A bio-oxidant fuel cell as in claim 3 which includes:
(a) at least one means for refueling said cell communicating at one end with said fuel electrolyte chamber and terminating subcutaneously at the other end.

5. A bio-oxidant fuel cell as in claim 4 which includes:
(a) at least two refueling means disposed to communicate with said fuel electrolyte chamber to permit rinsing, filling, emptying and refilling of fuel/electrolyte composition.

6. A bio-oxidant fuel cell as in claim 5 wherein:
(a) said refueling means terminates subcutaneously in a port, pierceably resealable by a hypodermic needle, for fueling and/or refueling of said cell.

7. A bio-oxidant fuel cell as in claim 4 wherein:
(a) said electrolyte buffer ionic strength is in the range of from about 0.3 M to about 1.0 M, that the pH is in the range of from about 7.0 to 7.8;
(b) said fuel to oxygen concentration ratio is in the range of from about 5000 to 1 to about 50,000 to 1;
(c) said anode is selected from Platinum, Palladium, Ruthenium, Rubidium, Iridium, Rainey Metal Catalysts, Nickel, alloys and mixtures thereof; and
(d) said cathode is selected from gold, silver, carbon, mixtures, and alloys thereof.

8. A bio-oxidant fuel cell as in claim 7 wherein:
(a) said fuel is selected from carbohydrates, non-toxic polyhydric alcohols, acetates, and mixtures thereof.

9. A bio-oxidant fuel cell as in claim 8 wherein:
(a) said fuel is selected from glucose, glycerol, sorbitol, and mixtures thereof.

10. A bio-oxidant fuel cell as in claim 9 wherein:
(a) said anode is platinum black;
(b) said cathode is carbon black;
(c) said fuel is glycerol;
(d) said buffer is $NaH_2PO_4$ in ionic strength of from about 0.3–0.6 M;
(e) said fuel/electrolyte concentration to $O_2$ is in the range of from 20,000 to 30,000; and
(f) said pH is about 7.4.

11. A bio-oxidant fuel cell as in claim 1 in association with similar cells, electrically connected in series, parallel or a combination thereof to provide greater power output.

12. Method of operation of a biologically acceptable, implantable prosthesis comprising the steps of:
(a) providing an electrically powered implantable prosthesis;
(b) providing a fuel cell as in claim 4 in electrical connection with said prosthesis;
(c) implanting said fuel cell and prosthesis in body tissue;
(d) percutaneously refueling said cell when the power output of said cell drops to a predetermined minimum amount as required by said prosthesis.

13. Method as in claim 12 wherein:
(a) said refueling includes evacuating said cell through one refueling means while permitting sterile gas into said cell via a second refueling means, and refilling said cell with fresh fuel/electrolyte composition through one refueling means while evacuating said gas from said second refueling means.

14. Method as in claim 12 wherein:
(a) said refueling step includes flushing spent fuel/electrolyte composition from said cell with an excess of fresh fuel/electrolyte composition, by providing exit of said spent composition from one of said refueling means, while simultaneously inletting fresh fuel/electrolyte through a second of said means.

* * * * *